United States Patent [19]

Elango et al.

[11] Patent Number: 5,322,948
[45] Date of Patent: Jun. 21, 1994

[54] PROCESS FOR PREPARING PYRIDINECARBOXYLIC ACID DERIVATIVES

[75] Inventors: Varadaraj Elango; Donald R. Larkin; John R. Fritch; Michael P. Bodman; Werner H. Mueller, all of Corpus Christi, Tex.; Bernard F. Gupton, Virginia Beach, Va.; John C. Saukaitis, East Greenwich, R.I.

[73] Assignee: Hoechst Celanese Corporation, Somerville, N.J.

[21] Appl. No.: 818,396

[22] Filed: Jan. 2, 1992

Related U.S. Application Data

[63] Continuation of Ser. No. 693,188, Apr. 29, 1991, abandoned, which is a continuation-in-part of Ser. No. 403,277, Aug. 31, 1989, abandoned.

[51] Int. Cl.⁵ .......................................... C07D 213/69
[52] U.S. Cl. ................................ 546/250; 544/332; 544/333; 546/169; 546/170
[58] Field of Search ................ 546/250, 169, 170; 544/332, 333

[56] References Cited

U.S. PATENT DOCUMENTS

| | | | |
|---|---|---|---|
| 4,009,174 | 2/1977 | Cluzan et al. | 260/293.69 |
| 4,656,283 | 4/1987 | Doehner, Jr. et al. | 546/170 |
| 4,675,432 | 6/1987 | Maulding | 560/44 |
| 4,723,011 | 2/1988 | Doehner, Jr. | 546/250 |
| 4,816,588 | 3/1989 | Rieker et al. | 546/321 |
| 4,871,859 | 10/1989 | Gupton et al. | 546/250 |
| 4,948,896 | 8/1990 | Nagao | 546/250 |

FOREIGN PATENT DOCUMENTS

| | | |
|---|---|---|
| 0274379 | 7/1988 | European Pat. Off. |
| 0325730 | 8/1989 | European Pat. Off. ... C07D 401/04 |
| 0415767 | 3/1991 | European Pat. Off. ........ C07D 213/803 |
| 0452094 | 10/1991 | European Pat. Off. ... C07C 239/18 |
| 1139566 | 6/1989 | Japan ......................... 546/250 |
| 8908103 | 9/1989 | World Int. Prop. O. ... C07D 213/55 |

OTHER PUBLICATIONS

Journal of Medicinal Chemistry, vol. 11, No. 1, 1968, Washington US, pp. 142–143, E. Falco et al. "N2-Hydroxyasparagine & 2-Hydroxylaminosuccinamide Hydrochloride".
Tetrahedron, (Inc. Tetrahedron Reports) vol. 40, No. 21, 1984, Oxford GB, pp. 4363–4370, J. E. Baldwin et al., "A General Procedure for the Synthesis of Isoxazolidin-5-ones".
Chemical Abstracts, vol. 92, No. 1, Jan. 7, 1980, Columbus, Ohio US; abstract No. 6888s, K. Basheeruddin et al., "A Convenient Synthesis of β-Amino Acid".
"Progress in the Chemistry of Organic Natural Products", Alves, L. F. et al., Springer-Verlag pp. 230, (1988).
"A Convenient Synthesis of β-Amino Acid", Bashceruddin, K. et al., Synthetic Communications, 9, 705–712 (1979).
"Synthetic Study of N-hydroxyaspartic Acid", Kolasa, T., Can. J. Chem., vol. 63, 2139, (1985).

Primary Examiner—Mary C. Lee
Assistant Examiner—Jacqueline Haley
Attorney, Agent, or Firm—Hugh C. Crall

[57] ABSTRACT

The present invention pertains to a method of preparing substituted and unsubstituted N-hydroxy-2-aminobutane diacid derivatives. The invention also pertains to the use of N-hydroxy-2-aminoethane derivatives (including the N-hydroxy-2-aminobutane diacid derivatives) in the preparation of pyridine derivatives.

41 Claims, No Drawings

PROCESS FOR PREPARING PYRIDINECARBOXYLIC ACID DERIVATIVES

This application is a continuation of prior U.S. application Ser. No. 07/693,188 Apr. 29, 1991, now abandoned and/which is a continuation-in-part of application Ser. No. 07/403,277 Aug. 31, 1989 now abandoned.

BACKGROUND OF THE INVENTION

2. Field of the Invention

The present invention pertains to a method for preparing pyridine derivatives by reacting substituted or unsubstituted unsaturated carboxylic acid derivatives with unsubstituted hydroxylamine and $\alpha,\beta$-unsaturated carbonyl compounds.

2. Background Art

N-hydroxyamino acids are valuable precursors for natural amino acids, peptides, herbicides, antibiotics, growth promoting agents, antitumor agents, antifungal agents, and polymers. It has been known that the addition of hydroxylamine to an unsaturated monocarboxylic acid derivative can be used to obtain N-hydroxyamino mono carboxylic acid derivative. However, addition of hydroxylamine to an unsaturated dicarboxylic acid, such as fumaric acid, in the presence of an enzyme does not successfully result in the isolation of N-hydroxyaspartic acid, as reported in "Progress in the Chemistry of Organic Natural Products", L. F. Alves et al., Springer-Verlag (1988), page 230. Indeed, the utilization of enzyme extracts, such as Bacillus caderas or proteus vulgaris also does not yield success in isolating this desired product, but resort must be made, through utilization of a benzyl group, to protect the hydroxylamine moiety as reported by Kolasa, Can. J. Chem., Vol. 63, 2139 (1985). Such methods are cumbersome and involve the removal of protecting groups rather than employing hydroxylamine or a salt thereof directly.

K. Bashceruddin et. al., Synthetic Communications, 9, 705–712 (1979) reports the questionable result of obtaining of N-hydroxyaspartic acids of greatly different melting points from maleic acid and fumaric acid, utilizing hydroxylamine. The reaction conditions for such conversion(s) are not disclosed, nor is revealed the criticality involved for obtaining N-hydroxyaspartic acid or its derivatives, namely a critical pH. Furthermore, the only relevant reaction conditions revealed in this publication, those for preparation of N-hydroxy-3-amino-3-(p-nitrophenyl)propionic acid from p-nitrocinnamic acid, do not yield N-hydroxyaspartic acid.

Literature methods for preparing 5,6-dialkyl and 5-alkyl-6-arylpyridine-2,3-dicarboxylic acids and esters are limited and often require oxidation of alkyl or aryl substituents at positions 2 and 3 in order to obtain diacids. Recently there has been disclosed a method for the preparation of substituted and disubstituted pyridine-2,3-dicarboxylic acid esters and 2-alkylnicotinates utilizing $\alpha$-halo-$\beta$-ketoesters and $\alpha,\beta$-unsaturated aldehydes or ketones in the presence of an ammonium salt. The use of $\alpha$-halo-$\beta$-ketoesters is not desired due to the fact that such materials are usually costly and unstable.

U.S. Pat. No. 4,723,011 discloses preparation of substituted and disubstituted pyridine-2,3-dicarboxylates by the reaction of an $\alpha$-halo-$\beta$-ketoester such as chlorodiethyloxalacetate (chloro-DOX) and an $\alpha,\beta$-unsaturated aldehyde or ketone such as 2-ethylacrolein in the presence of at least 2 molar equivalents of an ammonium salt in order to produce the desired compounds.

U.S. Pat. No. 4,816,588 discloses and claims a process for preparing pyridine-2,3-dicarboxylic acids by the oxidation of 8-substituted quinolines.

European patent application 274,379 published Jul. 13, 1988 discloses two processes for producing pyridine-2,3-dicarboxylic acid compounds. One process seems similar to that previously described in U.S. Pat. No. 4,723,011 and the other process involves reacting on $\alpha,\beta$-unsaturated aldehyde or ketone with various aminomaleates or aminofumarates such as diethyl aminomaleate.

European patent application 299,362 published Jan. 18, 1989 also discloses the same reaction.

U.S. Pat. No. 4,675,432 to Donald R. Maulding, issued Jun. 23, 1987 described a method for the preparation of anilinofumarate. A dichlorosuccinate is reacted with a molar equivalent of aniline in an inert organic solvent and with two or more molar equivalents of an aqueous base in the presence of a phase transfer catalyst to produce the anilinofumerate.

U.S. Pat. No. 4,656,283 to Robert F. Doehner, Jr., issued Apr. 7, 1987 describes a method for the preparation of alkyl esters of substituted 2-methylquinoline-3-carboxylic acid and quinoline-2,3-dicarboxylic acid as well as dialkyl 3-(substituted)-phenylaminobut-2-enedioates. An appropriately substituted aniline is reacted with approximately an equimolar amount of a keto-ester to produce the products above-described.

Although the methods above-described are effective, nevertheless, because of the commercial importance of the compounds, particularly as useful intermediates for the preparation of herbicidal 2-(2-imidazolin-2-yl)nicotinic acids, esters and salts, any improvement in the process is of tremendous potential economic significance.

SUMMARY OF THE INVENTION

The present invention pertains to a method of preparing substituted and unsubstituted N-hydroxy-2-aminobutane diacid derivatives which can be converted to pyridine derivatives. To produce pyridine derivatives, an unsubstituted hydroxylamine is reacted with an substituted or unsubstituted unsaturated carboxylic acid derivative to produce N-hydroxyethane derivatives which are reacted with $\alpha,\beta$-unsaturated carbonyl compounds. In the alternative, a single pot reaction can be carried out wherein the unsubstituted hydroxylamine is contacted with a substituted or unsubstituted unsaturated carboxylic acid derivative, followed by subsequent addition of the $\alpha,\beta$-unsaturated carbonyl compound, to produce the pyridine derivative.

The chemical formulae representing the above-described method are shown below:

I. Synthesis of N-Hydroxy-2-aminobutane Diacid Derivatives

In accordance with the present invention, in preparation of the substituted and unsubstituted N-hydroxy-2-aminobutane diacid derivatives, it was discovered that the pH of the reaction medium is critical, and should range from about 5 to about 12 and preferably from about 6.5 to about 9. In addition, the present invention permits reaction at ambient temperatures (about 25° C.) to about 80° C., whereby reaction products which tend to be thermally unstable at higher temperatures are preserved.

The reaction is represented by the following formulae:

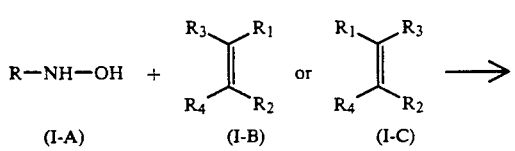

(I-A)    (I-B)    (I-C)

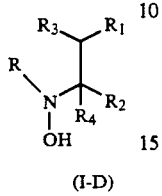

(I-D)

wherein R=H, alkyl (preferably $C_1$-$C_6$ straight or branched), substituted or unsubstituted aryl (preferably phenyl or naphthyl), and wherein the substituents are selected from alkyl, alkoxy, carboxy, halogen, cyano, and nitro;

wherein $R_1$ and $R_2$=each independently,

wherein Z is $OR_5$ or $NR_5R_6$; or CN; or
wherein $R_1$ and $R_2$ together is

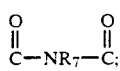

wherein $R_3$ and $R_4$ are each independently H; alkyl; halogen; CN; substituted or unsubstituted aryl (preferably phenyl and naphthyl) wherein the substituents are selected from alkyl, arylalkyl, alkoxy, carboxy, halogen, nitro, and cyano; and

wherein Z is defined as above;
wherein $R_5$ and $R_6$ are each independently H, alkyl (preferably $C_1$-$C_6$ straight or branched), aryl (preferably phenyl), arylalkyl (preferably aryl $C_1$-$C_6$ alkyl); or wherein $R_5$ and $R_6$ together with the nitrogen atom form a heterocyclic substituent, selected from pyrrolidinyl, piperidinyl, imidazolidyl, hydrogenated pyrimidinyl, including dihydro-, tetrahydro-, and hexahydropyrimidinyl; and wherein $R_7$ is H, alkyl (preferably $C_1$-$C_6$ straight or branched), substituted or unsubstituted aryl (preferably phenyl), or an alkoxy of 1-6 carbon atoms.

II. Preparation of Pyridine Derivatives from N-Hydroxy-2-aminoethane Derivatives It has now been found that N-hydroxy-2-aminoethane derivatives of Formula I-D, wherein R is H, can be reacted with an α,β-unsaturated carbonyl compound to yield pyridinecarboxylic acid derivatives of Formula II

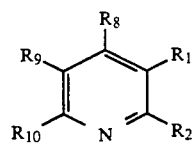

wherein $R_1$ and $R_2$ are each independently

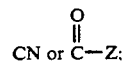

or wherein one of $R_1$ and $R_2$ is CN or

and the other of $R_1$ and $R_2$ is H, alkyl, aryl; or wherein $R_1$ and $R_2$ together is $$\overset{O}{\underset{}{\|}}C-NR_7-\overset{O}{\underset{}{\|}}C;$$

wherein Z is $OR_5$ or $NR_5R_6$;
wherein $R_5$ and $R_6$ are each independently H, alkyl, aryl, arylalkyl, or $R_5$ and $R_6$ together with the nitrogen atom form a heterocyclic substituent selected from pyrrolidinyl, piperidinyl, imidazolidyl, and hydrogenated pyrimidinyl; wherein $R_7$ is H, alkyl, aryl (preferably phenyl), or alkoxy;
wherein $R_8$ and $R_{10}$ are H; $C_1$-$C_6$ alkyl; or $C_1$-$C_6$ straight or branched alkenyl; or aryl which may be substituted with a substituent selected from alkyl, alkoxy, carboxy, carboalkoxy, halogen, and cyano;
wherein $R_9$ is the same as $R_8$ and $R_{10}$ above, but also including halogen, and
wherein $R_9$ and $R_{10}$ taken together can be —$(CH_2)$—$_{3-10}$.

The expression aryl is preferably intended to mean substituted or unsubstituted aryl unless otherwise defined; the substitution can be in one or more positions. The expression aryl is preferably intended to mean phenyl or naphthyl unless otherwise defined. The expression alkyl is preferably intended to mean straight or branched $C_1$-$C_6$ unless otherwise defined.

The N-hydroxyamino derivatives useful in the novel process of this invention are those of the Formula I-D, wherein R=H, see Formula I-E below:

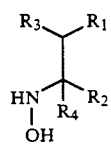

wherein $R_1$ and $R_2$ are as described above;
wherein $R_3$ is hydrogen or halogen; and
wherein $R_4$ is hydrogen.

The α,β-unsaturated carbonyl compounds useful in the novel process of this invention are those of the Formula III

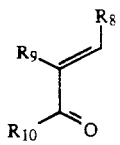

(III)

wherein $R_8$ and $R_{10}$=H, alkyl or alkenyl (preferably $C_1$-$C_6$ straight or branched) or substituted or unsubstituted aryl (preferably phenyl or naphthyl), wherein the substituents are selected from alkyl, alkoxy, carboxy, carboalkoxy, halogen, and cyano;

wherein $R_9$=the same as $R_8$ and $R_{10}$, but also including halogen, and wherein $R_9$ and $R_{10}$ taken together can be —$(CH_2)$—$_{3-10}$.

Throughout the specification and appended claims, a given chemical formula or name shall encompass all geometric, optical isomers and racemic mixtures thereof where such isomers exist.

In the above definitions, the term "aryl" refers to a monovalent substituent which consists of an aryl group, e.g. phenyl, o-toluyl, m-methoxyphenyl, etc., of the

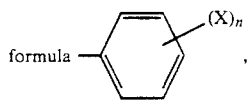

where X is hydrogen, halogen, lower alkyl, lower alkoxy, $CF_3$, and $NO_2$ and n is an integer of 1 to 5; the term "arylalkyl" refers to a monovalent substituent which consists of an aryl group, e.g. phenyl, o-toluyl, m-methoxyphenyl, etc., linked through an alkylene group having its free valence bond from a carbon of the lower alkylene group, and having a formula of

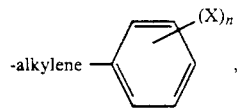

where X and n are is as defined above; the term "alkylene" refers to a bivalent radical of the lower branched or unbranched alkyl group it is derived from having valence bonds from two terminal carbons thereof, e.g. ethylene (—$CH_2CH_2$—), propylene (—$CH_2CH_2CH_2$—), isopropylene ($CH_3CH$—$CH_2$—), etc; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.

In the alternative:

III. Single Pot Formation of the Pyridine Derivative from Substituted or Unsubstituted Unsaturated Carboxylic Acid Derivatives, Unsubstituted Hydroxylamine, and α,β-Unsubstituted Carbonyl Compounds

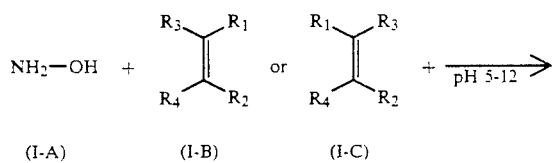

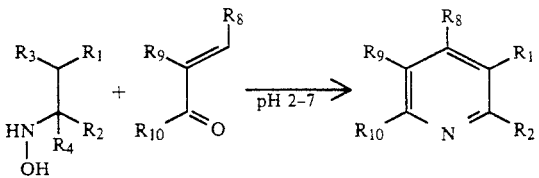

wherein R=H;
wherein $R_1$ and $R_2$ are each independently CN or

or wherein one of $R_1$ and $R_2$ is CN or

and the other of $R_1$ and $R_2$ is H, alkyl, aryl; wherein $R_1$ and $R_2$ together is

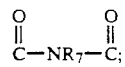

wherein Z is $OR_5$ or $NR_5R_6$; wherein $R_5$ and $R_6$ are each independently H, alkyl, aryl, arylalkyl, or $R_5$ and $R_6$ together with the nitrogen atom form a heterocyclic substituent selected from pyrrolidinyl, piperidinyl, imidazolidyl, and hydrogenated pyrimidinyl; wherein $R_7$ is H, alkyl, aryl (preferably phenyl), or alkoxy; wherein $R_8$ and $R_{10}$ are H; alkyl, or $C_1$-$C_6$ straight or branched alkenyl; or substituted or unsubstituted phenyl or naphthyl, wherein said substituent is selected from alkyl, alkoxy, carboxy, carboalkoxy, halogen, and cyano; wherein $R_9$ is the same as $R_8$ and $R_{10}$ above, but also including halogen, and $R_9$ and $R_{10}$ taken together can be —$(CH_2)$—$_{3-10}$.

The α,β-unsaturated carbonyl compounds are preferably aldehyde or ketone wherein $R_8$, $R_9$, and $R_{10}$ are as described above.

The acetal and ketal derivatives of the carbonyl compounds, or the Mannich base equivalent to such carbonyl compounds can also be used in the invention.

DETAILED DESCRIPTION

More specifically, the preferred embodiments of the above-described method follow. Throughout the specification and appended claims, a given chemical formula or name shall encompass all geometric, optical isomers and racemic mixtures thereof where such isomers exist.

I. Synthesis of N-Hydroxy-2-aminobutane Dicarboxylic Acid Derivatives

The present invention is described in terms of synthesizing esters of N-hydroxyaspartic acid. However, it should be understood that such description is exemplary only and is for purposes of exposition and not for purposes of limitation. It will be readily appreciated that the inventive concept described is equally applicable to both substituted and unsubstituted N-hydroxyaspartates as well as esters which are alkyl or aryl.

This embodiment of the present invention relates to a method of synthesizing a N-hydroxyaspartic acid derivative of the formula:

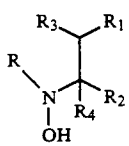 (I-D)

where $R_1$ and $R_2$ are each independently

where Z is $OR_5$ or $NR_5R_6$ where $R_5$ and $R_6$ are each independently H, alkyl (preferably $C_1$-$C_6$ alkyl branched or straight), aryl (preferably phenyl or naphthyl), arylalkyl, or $R_5$ and $R_6$ together with the nitrogen atom form a heterocyclic substituent, selected from pyrrolidinyl, piperidinyl, imidazolidyl, hydrogenated pyrimidinyl, including dihydro-, tetrahydro-, and hexahydropyrimidinyl; CN, or $R_1$ and $R_3$ together is

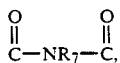

where $R_7$ is as defined above; and $R_3$ and $R_4$ are each independently H, alkyl (preferably $C_1$-$C_6$ alkyl branched or straight), aryl (preferably phenyl or naphthyl), arylalkyl,

where Z is as defined above; CN, and halogen.

The term "alkyl" refers to a straight or branched chain hydrocarbon of 1 to 18 carbon atoms containing no unsaturation, e.g. methyl, ethyl, isopropyl, 2-butyl, neopentyl, n-hexyl, n-heptyl, n-nonyl, etc.; the term "aryl" refers to a monovalent substituent which consists of an aryl group, e.g. phenyl, o-toluyl, m-methoxyphenyl, etc., of the formula

where X is hydrogen, halogen, lower alkyl, lower alkoxy, $CF_3$, and $NO_2$, and n is an integer of 1 to 5; the term "arylalkyl" refers to a monovalent substituent which consists of an aryl group, e.g. phenyl, o-toluyl, m-methoxyphenyl, etc., linked through an alkylene group having its free valence bond from a carbon of the lower alkylene group, and having a formula of

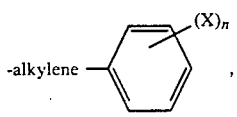

where X and n are is as defined above; the term "alkylene" refers to a bivalent radical of the lower branched or unbranched alkyl group it is derived from having valence bonds from two terminal carbons thereof, e.g. ethylene (—$CH_2CH_2$—),

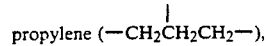

isopropylene, etc; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.

The synthesis of N-hydroxyaspartic acid derivative (Compound I-D, when R is H) is made in the following manner. The substituents $R_1$, $R_2$, $R_3$, $R_4$, $R_5$, $R_6$, and Z are as defined above unless indicated otherwise.

A suitable diacid derivative of the formula

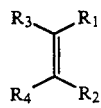 (I-B)

or

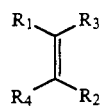 (I-C)

is selected. Such diacid derivatives are well known or can be synthesized using conventional techniques well known to those of ordinary skill in the art. Compound I-B or I-C is reacted with substituted hydroxylamine R—NH—OH or with unsubstituted hydroxylamine, H—NH—OH, or a suitable salt thereof, to produce N-hydroxyaspartic acid derivative. For purposes of simplification, subsequent descriptions will be limited to unsubstituted hydroxylamine, although it is understood the hydroxylamine can be substituted as well. A suitable hydroxylamine salt includes a mineral acid salt such as hydroxylamine hydrochloride, hydroxylamine sulfate, hydroxylamine bisulfate, hydroxylamine phosphate etc. or an organic acid salt, e.g. hydroxylamine acetate, etc. The reaction may be carried out with or without a suitable solvent. If carried out in a solvent, a suitable solvent includes water, a lower alkanol, e.g. methanol, ethanol, isopropanol, 1-butanol, etc.; a halogenated lower hydrocarbon or alkane e.g. dichloromethane, chloroform, carbontetrachloride, dichloromethane etc.; an aromatic hydrocarbon, etc.; benzene, toluene, etc.; and ether, e.g. ethylether, dioxane, tetrahydrofuran, etc.; an ester, e.g. ethyl acetate, isopropyl acetate, butyl acetate, etc.; and an aprotic solvent, e.g. acetonitrile, dimethylformamide, dimethylsulfoxide, etc; and mixtures thereof.

It is critical that the reaction be conducted under weakly acidic to basic conditions (pH=5-12) since it has been found that when the corresponding dicarboxylic acid of Compound I-B or I-C is employed, e.g. maleic acid or fumaric acid, addition of the hydroxylamine across the double bond leading to the N-hydroxyaspartic acid does not occur. Additionally, where the reaction between Compound I-B or I-C and the hydroxylamine or its salt is conducted under more acidic pH conditions, the desired reaction again does not occur to yield the N-hydroxyaspartic acid derivative. The reaction must be carried out under critical pH conditions which are at most weakly acidic, i.e. the upper acid pH range being weakly acid, that is, at a pH region of 5 through about 12, preferably a pH range of about 6.5 to about 9.

During the reaction of hydroxylamine with Compound I-B or I-C, the hydroxylamine itself provides the basic medium. When a hydroxylamine salt is used, a suitable base should be employed to achieve the critical pH reaction condition. A suitable base is one selected from an inorganic base, e.g. sodium hydroxide, potassium hydroxide, ammonium hydroxide, sodium carbonate, potassium carbonate etc.; an organic base, e.g. pyridine, triethylamine, sodium methoxide, etc., present in an amount ranging from about 1 to about 3 moles of base to one mole of hydroxylamine salt, and preferably from 1 mole of base per one mole of hydroxylamine salt, except in the case of a hydroxylamine salt of a diprotic acid, such as hydroxylamine sulfate, wherein 2 moles of base per mole of salt is preferred.

The hydroxylamine can be supplied in the form of a solution which permits one to carry out the reaction between the hydroxylamine and an unsaturated carboxylic acid derivative in a homogeneous solution. This increases the efficiency of formation of the N-hydroxyaminoethane derivatives. Such a solution of hydroxylamine is prepared by reacting a salt of hydroxylamine with an inorganic base and then adding an organic solvent which precipitates the inorganic salt reaction product which is removed by filtration, leaving a solution of the hydroxylamine in the organic solvent.

For example, not by way of limitation, salts of hydroxylamine which can be used as described above include, but are not limited to, hydroxylamine sulfate, hydroxylamine hydrochloride, and hydroxylamine phosphate. The inorganic base which can be used is selected, not by way of limitation, from inorganic bases such as sodium hydroxide, potassium hydroxide, ammonium hydroxide, sodium carbonate, and potassium carbonate. Also for example, not by way of limitation, the organic solvents which can be used to precipitate the inorganic salt reaction product and form the hydroxylamine solution include, but are not limited to, $C_1-C_4$ alcohols (such as methanol, ethanol and propanol), ethers (such as tetrahydrofuran and dioxane), esters (such as ethyl acetate and isopropyl acetate), and aprotic solvents (such as acetonitrile and dimethylformamide).

It is to be understood that pH values, resulting when there are solvent levelling effects involved, which correspond to the above-identified critical pH range are equally applicable.

Compound I-B or I-C and the hydroxylamine or its salt, are employed in a mole ration ranging from about 1:1 to about 1:3, with the preferred mole ratio being between 1:1 to 1:1.5 of Compound I-B or I-C to the hydroxylamine or its salt.

Typically the reaction, conducted with the mole ratios of Compound I-B or I-C, hydroxylamine or its salt, and base, as indicated above, is carried out at a temperature ranging between about −10° C. to about 80° C., preferably about 10° C. to about 50° C., for a time period ranging from about 0.1 to about 15 hours to obtain addition of the $NH_2OH$ (or RNHOH) across the carbon-carbon double bond of Compound I-B or I-C, typically following Markovnikov's rule, to obtain Compound I-E (or Compound I-D).

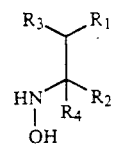
(I-E)

Compound I-E includes, but is not limited to, dimethyl N-hydroxyaspartate, diethyl N-hydroxyaspartate, dipropyl N-hydroxyaspartate, di-iso-propyl N-hydroxyaspartate, di-n-butyl N-hydroxyaspartate, N-hydroxyaspartonitrile and triethyl 2-(N-hydroxyamino)-ethane-1,1,2-tricarboxylate.

If Compound I-D is an ester, of course it can be hydrolyzed, using conventional techniques, to obtain the free acid, i.e.

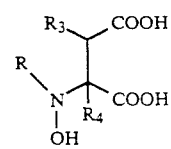
(I-F)

The examples which follow are for purposes of illustrating the embodiment of the present method described under I above, and are not to be construed as limiting the invention disclosed herein.

EXAMPLE 1

Diethyl N-Hydroxyaspartate

Hydroxylamine free base (50% aqueous solution, 45.0 g, 0.68 mol) was added dropwise to diethyl maleate (100.0 g, 0.56 mol) under nitrogen. The reaction temperature was maintained below 55° C. with an ice bath. The mixture was stirred for 30 minutes. Dichloromethane (100 ml) was added to the reaction mixture and the organic layer was collected and dried using anhydrous magnesium sulfate. The organic layer was concentrated under reduced pressure to give crude diethyl N-hydroxyaspartate (103 g, 89% yield). The product was analyzed by NMR spectroscopy and found to be greater than 95% pure.

EXAMPLE 2

Diethyl N-Hydroxyaspartate

Sodium hydroxide (40% aqueous solution, 12.9 g, 0.129 mol) was added over 20 minutes to a stirred mixture of diethyl maleate (17.3 g, 0.1 mol) and hydroxylamine sulfate (25% aqueous, 39.0 g, 0.059 mol) during which the reaction temperature rose from 28° C. to 53° C. The reaction mixture was stirred for 30 minutes under nitrogen. The mixture was transferred to separating funnel, methylene chloride was added (50 ml), the organic layer was collected dried using anhydrous magnesium sulfate, and concentrated to give diethyl N-hydroxyaspartate (18.5 g, 0.99 mol, 90% yield).

EXAMPLE 3

Diethyl N-Hydroxyaspartate

Sodium hydroxide solution (50% aqueous, 96.0 g, 1.2 mol) was added over 30 minutes to an aqueous solution of hydroxylamine sulfate (25%, 394.2 g, 0.6 mol). The temperature was kept below 40° C. during the caustic addition. The reaction pH was about 9 at the end of caustic addition.

Diethyl maleate (172.0 g, 1.0 mol) was then added to the reaction and stirred for 60 minutes at which time the pH was about 7.4. The reaction mixture was transferred to a separatory funnel, the layers were allowed to separate, and the organic phase containing diethyl N-hydroxyaspartate was separated. The crude product was analyzed by NMR and found to be >90% pure (207 g).

EXAMPLE 4

Preparation of Diethyl N-hydroxyaspartate

Hydroxylamine Free base (50% aqueous solution, 45.0 g, 0.68 mol) was added dropwise to a solution of diethyl maleate (100.0 g, 0.56 mol) in ethanol (100 mL) in a 3-neck flask blanketed with nitrogen. The reaction temperature was maintained below 55° C. with an ice bath. The mixture was stirred for 30 minutes. The reaction mixture was concentrated under reduced pressure to give crude diethyl N-hydroxyaspartate (103 g, 89% yield). The product was analyzed by nuclear magnetic resonance spectroscopy (NMR) and shown to be at least 95% pure. NMR (acetone-d6) 1.20 (m, 6H), 2.59 (dd, J 6.8, 16.1 Hz, 1H), 2.76 (dd, J 6.8, 16.1 Hz, 1H), 3.89 (t, J 6.8 Hz, 1H), and 4.11 (m, 4H).

EXAMPLE 5

Dimethyl N-Hydroxyaspartate

Hydroxylamine free base (50% aqueous solution, 7.3 g, 0.11 mol) was added over a 30 minute period to dimethyl maleate (15.0 g, 0.1 mol) under nitrogen. The reaction temperature was maintained below 55° C. with an ice bath. The mixture was stirred for 30 minutes. The reaction mixture was added to dichloromethane (200 ml) and the organic phase was separated. The organic phase was dried with magnesium sulfate and concentrated to give dimethyl N-hydroxyasparate (16.2 g, 90% yield).

EXAMPLE 6

Dibutyl N-Hydroxyaspartate

Hydroxylamine free base (50% aqueous solution, 8.0 g, 0.12 mol) was added dropwise to dibutyl maleate (25.0 g, 0.1 mol) in a 3-neck 250 ml flask blanketed with nitrogen. The reaction temperature was maintained below 55° C. with an ice bath. The mixture was stirred for 30 minutes. The gas liquid chromatography (GLC) analysis of the reaction mixture indicated 96% conversion of dibutyl maleate. The NMR analysis showed that the reaction mixture contained dibutyl N-hydroxyaspartate in greater than 95% purity.

EXAMPLE 7

Preparation of Diethyl N-Hydroxyaspartate Using Ethanol to Produce a Homogeneous Reaction Mixture A solution of 394.4 g (0.60 mols; 1.20 eq) of 25% aqueous hydroxylamine sulfate was placed in a 2-liter round-bottom flask equipped with a reflux condenser, thermometer, dropping funnel, mechanical stirrer, and cooling bath. To this was added, over about a thirty minute period, 94.1 g (1.20 mole) of 50% aqueous sodium hydroxide. Phenolphthalein indicator was added and the last of the caustic was added dropwise to the end point (pH of ~9.5). The temperature was kept below 40° C. Then 400 ml of ethanol was added; the sodium sulfate reaction product, which precipitated upon addition of the ethanol, was removed by filtration. Then 172.0 g (1 mole) of diethyl maleate was added to the ethanol-hydroxylamine solution, and the resulting homogeneous solution was stirred for 30 minutes. This latter reaction produced diethyl N-hydroxyaspartate in quantitative yield (>99%).

EXAMPLE 8

N-Hydroxyaspartonitrile

Hydroxylamine free base (50% aqueous solution, 2.0 g, 30.3 mmol) was added over 2 minutes to a suspension of fumaronitrile (2.0 g, 25.6 mmol) in ethanol (15.0 g). During the course of the hydroxylamine addition, the reaction temperature changed from 18° C. to 48° C. The reaction mixture was cooled to room temperature and stirred for one hour. The GLC analysis of the reaction mixture showed that the reaction proceeded with complete conversion of fumaronitrile to give N-hydroxyaspartonitrile in 90% selectivity. The solvent was removed and the product was characterized by NMR.

EXAMPLE 9

Triethyl 2-(N-hydroxyamino)-1,1,2-ethanetricarboxylate or Diethyl 3-(Carboethoxy)-N-hydroxyaspartate Triethyl ethenetricarboxylate (4.0 g, 16.3 mmol), obtained from diethyl malonate and ethyl glyoxalate, was dissolved in ethanol (25 g) and hydroxylamine (50% aqueous solution, 1.3 g, 19.6 mmol) was added to the reaction mixture. A solid precipitated out within 10 minutes indicating the completion of the reaction. The solvent was removed under reduced pressure to give the crude product. The crude product was analyzed by NMR and found to have triethyl 2-(N-hydroxyamino)ethanetricarboxylate.

EXAMPLE 10

Diethyl N-Phenyl-N-hydroxyaspartate

Diethylmaleate (7.7 g, 0.045 mole) was added to a mixture containing 5.0 g (0.046 mole) N-phenylhydroxylamine in 7.66 g of absolute ethanol. The mixture was allowed to stir for 15 hours at room temperature. GC analysis showed a trace of diethylmaleate remaining. 1.0 g of Norite and 10 mL of ethanol were then added to the reaction mixture. The mixture was allowed to stir for 10 minutes and then filtered free of the carbon. The carbon was washed with additional ethanol. The filtrate was evaporated under high vacuum temperature to give an oil which crystallized upon cooling in a dry ice/acetone bath. 11.9 g of product was obtained after drying in vacuum desicator at room temperature under high vacuum, the product mp was 50°-53° C.

EXAMPLE 11

Preparation of Diethyl N-Phenyl-N-Hydroxyaspartate

A solution of diethyl maleate (20.65 g, 0.117 mol) in ethanol (25.0 g) was added dropwise to a solution of N-phenylhydroxylamine (14.6 g, 0.129 mol) in ethanol (46.3 g). The reaction mixture was stirred at room temperature for an hour. The analysis of the reaction mixture by thin layer chromatography indicated the completion of the reaction. The reaction mixture was concentrated under reduced pressure to give the crude product (37.46 g). The crude product was crystallized from ethylacetate-hexane (28.0 g, 85.0% yield).

II. Conversion of the N-Hydroxy-2-Aminoethane Derivative to Pyridine Derivatives Compound I-E is then reacted with a substituted α,β-unsaturated carbonyl compound of the formula

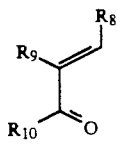

where $R_8$, $R_9$, and $R_{10}$ are as defined above, to obtain a compound of the formula

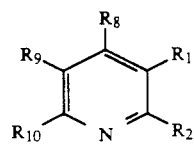

which includes 2,3-pyridinedicarboxylic acid derivatives such as 5-alkylpyridine-2,3-dicarboxylic acid.

The reaction between the compounds of Formula I-D and those of Formula III is conveniently carried out by heating the same in the presence of an acid, at a temperature ranging from about 25° C. to about 150° C., for periods of time ranging from about 0.5 to about 48 hours. The reaction can also be carried out in the presence of a suitable solvent, preferably at the reflux temperature of the solvent. Although the preferred temperature is at reflux, any temperature from ambient up to the boiling point of the solvent can be employed. A relative pH between 3-4 appears optimal although a pH ranging from 2-7 can be used.

The mole ratio of the compounds of Formula I-D to the α,β-unsaturated carbonyl compounds ketones of Formula III is not critical and can range from about 1:3 to 3:1. It is preferred to use approximately from 1:10 to 1:1.5 molar ratios.

If desired a dehydrogenation catalyst can be added to the reaction mixture of in order to aid in aromatization of the newly-generated ring. The dehydrogenation catalyst when employed is conventional in the art and includes metals or compounds of platinum, palladium, ruthenium, iridium, nickel, iron, copper, cobalt, rhodium, etc. The dehydrogenation metal or compound thereof deposited on a suitable support, such as alumina, carbon, clay, zeolites, chromia, zirconia, etc. A preferred dehydrogenation catalyst is palladium on carbon.

As has been previously stated, an acid is employed to provide an acidic pH range (from about 2 to about 7). Suitable acids include inorganic acids such as hydrochloric, phosphoric, sulfuric, etc. and preferably organic acids such as acetic, trifluoroacetic, p-toluenesulfonic, methanesulfonic, trifluoromethanesulfonic, propionic, butyric or other carboxylic acids including aromatic carboxylic acids. Ion-exchange resins such as Amberlyst ®, Dowex ®, NAFION ® can also be used as acidic components.

When an acid is used which is also a solvent i.e. acetic acid, no additional solvent is required.

Solvents suitable for use in the method of this invention include: water, alcohols, chlorinated hydrocarbons, hydrocarbons, aromatic hydrocarbons, ethers, organic acids, esters, and aprotic solvents such as acetonitrile. The preferred solvents are lower alkyl alcohols, such as methanol, ethanol, propanol, and butanol and aromatic hydrocarbons, such as benzene and toluene. Particularly preferred solvents are 1-butanol, ethanol, or toluene.

Thus, pyridinecarboxylic acid derivatives containing substituents in the 4-,5- and 6-position may conveniently be prepared by admixing Formula I-E N-hydroxyamino derivatives with a Formula III α,β-unsaturated aldehyde or ketone in the presence of an acid and preferably a solvent, and stirring the resulting reaction mixture at a temperature in the range of ambient temperature to the boiling point of the solvent, and preferably at reflux, until the reaction is essentially complete and isolating the formed 4-substituted, 4,5-disubstituted, 4,6-disubstituted, 5-substituted, 6-substituted or 5,6-disubstituted pyridine-2,3-dicarboxylic acid derivatives by standard laboratory techniques such as extraction, evaporation, distillation or column chromatography.

Compound II, which includes 2,3-pyridine carboxylic acid derivatives, can be reacted with a 2-aminoalkane carboxamide (as defined in U.S. Pat. No. 4,758,667) under essentially anhydrous conditions, as described in this patent to form the 2-(imidazolin-2-yl)-3-pyridine carboxylic acids described therein. In the alternative, the 2,3-pyridine carboxylic acid derivatives can also be reacted with an aminonitrile under essentially anhydrous conditions to form 2-(imidazolin-2-yl)-3-pyridine carboxylic acids.

The Examples which follow are for purposes of illustrating the embodiment of the present method described under II above, and are not to be construed as limiting the invention disclosed herein.

EXAMPLE 12

Preparation of Diethyl 5-Ethylpyridine-2,3-dicarboxylate (5-EPDC) from Diethyl N-Hydroxyaspartate Diethyl N-hydroxyaspartate (20.2 g, 0.1 mol) was dissolved in Benzene (100 mL) and stirred under nitrogen. Trifluoroacetic acid (2.0 g, 0.018 mol) and 2-ethylacrolein (9.8 g, 0.11 mol) were added and the reaction mixture was stirred at 72°-75° C. for 16 hours. The reaction mixture was concentrated under reduced pressure to give crude diethyl 5-EPDC (27.92 g). The gas-liquid chromatographic (GLC) analysis of the crude product indicated that the reaction had proceeded with 91% conversion (based on diethyl maleate) and 41% yield (based on external standard) to diethyl 5-EPDC.

EXAMPLE 13

Preparation of Diethyl 5-EPDC from Diethyl N-Hydroxyaspartate

Diethyl N-hydroxyaspartate (20.2 g, 0.1 mol) was dissolved in ethanol (38 mL) and stirred under nitrogen. Acetic acid (5.1 g, 0.085 mol) and 2-ethylacrolein (10.05 g, 0.12 mol) were added and the reaction mixture was stirred at reflux for 6 hours. The reaction mixture was concentrated under reduced pressure to give crude diethyl 5-EPDC (25.6 g). The GLC analysis of the crude product indicated that the reaction had proceeded with 94% conversion and 47% yield.

EXAMPLES 14–19

Preparation of Esters of Substituted Nicotinic Acids by the Hydroxylamine Sulfate-Ethanol (HAS/EtOH) Method All esters of nicotinic acid shown in Table I below were prepared using the hydroxylamine sulfate-ethanol method.

Hydroxylamine Sulfate-Ethanol (HAS/EtOH) Method

A mixture was prepared from 25% aqueous hydroxylammonium sulfate (39.0 g, 0.060 mol) and 50% aqueous sodium hydroxide (9.6 g, 0.12 mol). 40 mL of ethanol was then added and the mixture was allowed to cool to room temperature and filtered to remove sodium sulfate. The filtered solution was placed in a 250-mL, 3-necked flask equipped with a reflux condenser, thermometer, heating mantle, stirrer, pH electrode, and dropping funnel. Then an $\alpha,\beta$-unsaturated ester (ethyl crotonate or ethyl acrylate) (0.10 mole) was added and the mixture was stirred at room temperature for 60 minutes. Then an $\alpha,\beta$-unsaturated carbonyl compound (0.125 mole) was added all at once. About 10 mL of acetic acid was added to lower the pH to below 4.0 and the reaction mixture was heated to reflux for 3 to 5 hours.

The reaction is represented by the following formulae:

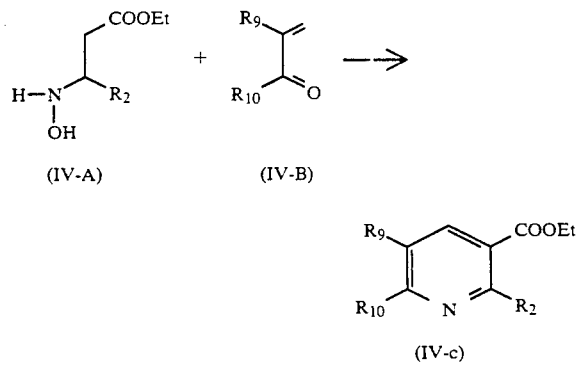

TABLE 1

| Example No. | $R_2$ | $R_9$ | $R_{10}$ | Yield, % |
|---|---|---|---|---|
| 14 | H | H | H | ~0 |
| 15 | H | $CH_3$ | H | ~5 |
| 16 | H | $CH_3CH_2$ | H | ~5 |
| 17 | $CH_3$ | H | H | ~5 |
| 18 | H | $CH_3$ | $CH_3$ | ~5 |
| 19 | H | $CH_3CH_2$ | $CH_3$ | ~5 |

III. Single Pot Formation of the Pyridine Derivative from Substituted or Unsubstituted Unsaturated Carboxylic Acid Derivatives, Unsubstituted Hydroxylamine, and $\alpha,\beta$-Unsaturated Carbonyl Compounds Another embodiment of the invention involves the single-pot preparation of substituted and disubstituted pyridinecarboxylates of Formula II by reacting a unsaturated carboxylic derivative of Formula I-B or I-C:

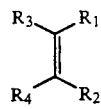

or

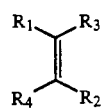

wherein $R_1$ and $R_2$ are each independently CN or

or wherein one of $R_1$ and $R_2$ is CN or

and the other of $R_1$ and $R_2$ is H, alkyl, aryl; or wherein $R_1$ and $R_2$ together is

wherein Z is $OR_5$ or $NR_5R_6$;
wherein $R_5$ and $R_6$ are each independently H, alkyl, aryl, arylalkyl, or $R_5$ and $R_6$ together with the nitrogen atom form a heterocyclic substituent selected from pyrrolidinyl, piperidinyl, imidazolidyl, and hydrogenated pyrimidinyl;
wherein $R_7$ is H, alkyl, aryl (preferably phenyl), or alkoxy; $R_3$ and $R_4$ are each independently H; alkyl; halogen; CN; substituted or unsubstituted aryl (preferably phenyl and naphthyl) wherein said substituents is selected from alkyl, arylalkyl, alkoxy, carboxy, halogen, nitro, and cyano;
with unsubstituted hydroxylamine of Formula (I-A) or a salt thereof, such as the hydrochloride salt, at ambient temperatures for periods of time ranging from about 30 minutes to about 3 hours at a pH ranging from about 5 to about 12, and preferably from 6.5 to 9. To the resulting reaction product, an acid is added to lower the pH to 2–7, or preferably 3–4, and an $\alpha,\beta$-unsaturated aldehyde or ketone of Formula III is added, and the reaction mixture is subjected to elevated temperatures ranging from about 25° C. to about 150° C. for periods of time ranging from about 1 to about 48 hours.

A preferred embodiment of the invention involves the preparation of substituted and disubstituted pyridinedicarboxylates of Formula II by treating a alkene of Formula I-B or I-C wherein $R_1$ and $R_2$ are defined above with a substituted or unsubstituted hydroxylamine or a mixture of a hydroxylamine salt and a base at a temperature of 15° C. to 60° C. for periods of 0.1 to 2 hours at a pH of 7–9. To the resulting reaction product is added sufficient acid to take the pH to 2–7, preferably 3–4, and preferably a solvent, is added. Then an $\alpha,\beta$-unsaturated carbonyl compound of Formula III is added, and the resulting mixture is stirred at a temperature in the range of ambient temperature to the boiling point of the solvent, until the reaction is essentially complete.

The reaction mixture is then cooled to ambient temperature of 20°–40° C. The product is concentrated under reduced pressure and can be purified by conventional techniques such as distillation, extraction, evaporation, or column chromatography.

If desired a dehydrogenation catalyst can be added to the reaction mixture.

The dehydrogenation catalyst when employed is conventional in the art and includes metals or compounds of platinum, palladium, ruthenium, iridium, nickel, iron, copper, cobalt, rhodium, etc. The dehydrogenation metal or compound thereof deposited on a suitable support, such as alumina, carbon, clay, zeolites, chromia, zirconia, etc. A preferred dehydrogenation catalyst is palladium on carbon.

When an acid is used which is also a solvent i.e. acetic acid, no additional solvent is required.

Solvents suitable for use in the method of this invention include: water, alcohols, chlorinated hydrocarbons, hydrocarbons, aromatic hydrocarbons, ethers, organic acids, esters, and aprotic solvents such as acetonitrile. The preferred solvents are lower alkyl alcohols, such as methanol, ethanol propanol, and butanol and aromatic hydrocarbons, such as benzene and toluene. The particularly preferred solvents are 1-butanol, ethanol, or toluene.

In another embodiment pyridine-2,3-dicarboxylic acid derivatives containing substituents in the 4-, 5- and 6-position may conveniently be prepared by reacting, at a neutral or slightly basic pH, a Formula I-B or I-C maleate or fumarate with a substituted or unsubstituted hydroxylamine or a salt thereof, then adding a Formula III $\alpha,\beta$-unsaturated aldehyde, or ketone, at a pH of 2-7 with an acid and preferably a solvent, and stirring the resulting reaction mixture at a temperature in the range of ambient temperature to the boiling point of the solvent, and preferably at reflux, until the reaction is essentially complete and isolating the formed 4-substituted, 4,5-disubstituted, 4,6-disubstituted, 5-substituted, 6-substituted or 5,6-disubstituted pyridine-2,3-dicarboxylic acid derivatives by standard laboratory techniques such as extraction, evaporation column chromatography, or distillation.

The amount of substituted or unsubstituted hydroxylamine or salt thereof used ranges from about 1 to about 1.5 mols of hydroxylamine per mol of said maleate or fumarate. Preferred ranges are about 1.0–1.2 mols.

If a hydroxylamine salt is used, a base such as sodium hydroxide, potassium hydroxide or ammonium hydroxide, in an amount of 1 to 2 moles, preferably 1 to 1.2 moles per mole of said hydroxylamine salt is needed to liberate the hydroxylamine.

The mole ratio of the alkene of Formula I-B and I-C to the $\alpha,\beta$-unsaturated carbonyl compound of Formula III is not narrowly critical and can range from about 1:3 to about 3:1. It is preferred to use approximately 1:1.0 to 1:1.5 molar ratios.

It is believed that the reaction of the I-B and I-C unsaturated carboxylic acid derivatives with the unsubstituted hydroxylamine or salt thereof inherently produces the N-hydroxyamino derivatives of Formula I-E. The hydroxylamine can be supplied in the form of a solution which permits one to carry out the reaction between the hydroxylamine and an unsaturated carboxylic acid derivative in a homogeneous solution. This increases the efficiency of formation of the N-hydroxyaminoethane derivatives. Such a solution of hydroxylamine is prepared by reacting a salt of hydroxylamine with an inorganic base and then adding an organic solvent which precipitates the inorganic salt reaction product which is removed by filtration, leaving a solution of the hydroxylamine in the organic solvent.

For example, not by way of limitation, salts of hydroxylamine which can be used as described above include, but are not limited to, hydroxylamine sulfate, hydroxylamine hydrochloride, and hydroxylamine phosphate. The inorganic base which can be used is selected from inorganic bases such as sodium hydroxide, potassium hydroxide, ammonium hydroxide, sodium carbonate, and potassium carbonate. Also for example, not by way of limitation, the organic solvents which can be used to precipitate the inorganic salt reaction product and form the hydroxylamine solution, but are not limited to $C_1$–$C_4$ alcohols (such as methanol, ethanol and propanol), ethers (such as tetrahydrofuran and dioxane), esters (such as ethyl acetate and isopropyl acetate), and aprotic solvents (such as acetonitrile and dimethylformamide).

In a preferred embodiment wherein the solution of hydroxylamine in an organic solvent is used as a reactant, a solution of hydroxylamine is prepared by reacting hydroxylamine sulfate and sodium hydroxide, followed by the addition of an alcohol such as ethanol. Addition of the ethanol precipitates sodium sulfate which is removed by filtration, leaving a filtrate solution of hydroxylamine in ethanol. Diethyl maleate is added to the filtrate solution, whereby a homogeneous reaction takes place to produce diethyl N-hydroxyaspartate. This is followed by an acid catalyzed reaction with 2-ethylacrolein to afford diethyl 5-ethylpyridine-2,3-dicarboxylate (diethyl 5-EPDC). The yields in laboratory scale work were at least 40–50% for diethyl 5-EPDC.

More generally, the solution of hydroxylamine can be reacted with an unsaturated carboxylic acid derivative to produce N-hydroxyaminoethane derivatives. The N-hydroxyaminoethane derivatives can then be reacted with a Compound III to produce pyridine derivatives of Formula II.

One of the preferred embodiments of the present invention pertains to the synthesis of 2,3-pyridine-dicarboxylic acid derivative of the formula

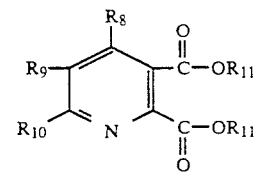

where $R_8$ is hydrogen or $C_1$–$C_6$ alkyl; $R_9$ is hydrogen, halogen, $C_1$–$C_6$ alkyl, $C_1$–$C_6$ hydroxyalkyl, $C_1$–$C_6$ alkoxy, phenyl or phenyl substituted-$C_1$–$C_6$ alkyl, or phenyl-$C_1$–$C_6$ alkyl, each substituted by $C_1$–$C_6$ alkyl, $C_1$–$C_6$ alkoxy or halogen; $R_9$ is hydrogen, $C_1$–$C_6$ alkyl, phenyl, phenyl-$C_1$–$C_6$ alkyl, or phenyl or phenyl $C_1$–$C_6$ alkyl each substituted by one $C_1$–$C_6$ alkoxy or halogen; $R_8$ and $R_9$ together are 1,3-butadienylene which can be substituted by halogen, $C_1$–$C_6$ alkyl, $C_1$–$C_6$ alkoxy, $C_1$–$C_6$ haloalkyl, $C_1$–$C_6$ alkylsulfonyl, nitro, cyano, phenyl, phenoxy, or phenyl or phenoxy, each substituted by one $C_1$–$C_6$ alkyl, $C_1$–$C_6$ alkyoxy or halogen, and $R_{11}$ is $C_1$–$C_8$ alkyl, phenyl or $C_1$–$C_6$ phenyl alkyl;

where embodiments of the compound of the preceding formula and $R_8$, $R_9$, and $R_{10}$ substituents are as revealed and defined as corresponding substituents $R_1$, $R_2$, $R_3$, and $R_6$ of U.S. Pat. No. 4,758,667, incorporated by reference hereinto in its entirety.

Such compounds can be used as a precursor in the synthesis of compounds of the formula

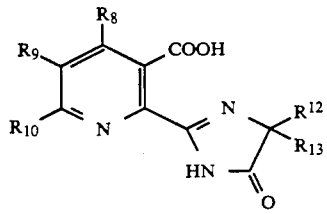

where $R_{12}$ and $R_{13}$ are each independently of the other $C_1$-$C_6$ alkyl, as revealed and defined as corresponding to substituents $R_4$ and $R_5$ in U.S. Pat. No. 4,758,667, incorporated hereinto by reference. The latter compound has herbicidal properties and can be used for controlling undesired plant growth.

The reactions described under Section III above are illustrated by the Examples which follow:

EXAMPLE 20

Preparation of Diethyl 5-EPDC from Diethyl Maleate, Hydroxylamine, and 2-Ethylarcolein Procedure without Pd/C Hydroxylamine free base (2.0 g, 0.031 mol) was added to a solution of diethylmaleate (4.3 g, 0.024 mol) in ethanol (15 mL) and the mixture was stirred for 30 minutes under nitrogen. The reaction products were analyzed by NMR and found to be 92% diethyl N-hydroxyaspartate. Trifluoracetic acid (1.0 g, 0.009 mol) and hexadecane (0.5 g, 0.0002 mol) were added, and the reaction mixture was heated to 70° C. 2-Ethylacrolein (2.7 g, 0.032 mol) was added and the reaction mixture was refluxed for 5 hours. The reaction mixture was cooled to room temperature and analyzed by GLC. The analysis showed that the reaction had proceeded with 92% conversion (based on diethyl maleate) and 52% selectivity to diethyl 5-EPDC (based on hexadecane as an internal standard). The solvent was removed under reduced pressure to give the crude product (8.2 g, 48% yield).

EXAMPLES 21-28

The procedure of Example 20 is repeated except that the following 2-aminobut-2-ene dioic acid derivatives and aldehydes or ketones are used:

| Aspartate | | | Aldehyde or Ketone | | |
|---|---|---|---|---|---|
| $R_{14}OOC-C(NH_2)=CH-COOR_{15}$ | | | $R_9-C(R_{10}-C=O)=CHR_8$ | | |
| | $R_{14}$ | $R_{15}$ | $R_9$ | $R_{10}$ | $R_8$ |
| Example 21 | methyl | propyl | H | H | phenyl |
| Example 22 | propyl | propyl | phenyl | ethyl | methyl |
| Example 23 | butyl | butyl | ethyl | methyl | H |
| Example 24 | ethyl | ethyl | methyl | H | H |
| Example 25 | ethyl | ethyl | H | methyl | H |
| Example 26 | ethyl | ethyl | H | H | methyl |
| Example 27 | ethyl | ethyl | —(CH$_2$)$_3$— | | H |
| Example 28 | ethyl | ethyl | —(CH$_2$)$_4$— | | H |

EXAMPLE 29

Synthesis of Diethyl 5-EPDC from Hydroxylamine Free Base Diethyl Maleate, and 2-Ethylacrolein Procedure with Pd/C Hydroxylamine free base (50% aqueous solution, 8.0 g, 0.118 mol) was added dropwise to diethyl maleate (17.1 g, 0.1 mol) in a 3-necked 250-mL flask blanketed with nitrogen. The reaction temperature was maintained below 55° C. with an ice bath. The mixture was stirred for 15 minutes, and then analyzed by NMR, which indicated 96% conversion of diethyl maleate to diethyl N-hydroxyaspartate. Ethanol (40.0 g), 2-ethylacrolein (10.0 g, 0.12 mol), trifluroacetic acid (7.0 g, 0.06 mol), and 5% Pd/C (0.22 g, 0.1 mmol) were successively added to the reaction mixture, which was then refluxed for 6 hours under nitrogen. The reaction mixture was cooled to room temperature, filtered through a small column of celite to remove Pd/C and concentrated under reduced pressure to give the crude product (32 g). The crude product was purified by distillation to give diethyl 5-EPDC.

EXAMPLE 30

Procedure with Acetic acid as Catalyst and Solvent

Hydroxylamine free base (50% aqueous solution, 8.0 g, 0.12 mol) was added to diethyl maleate (17.8 g, 0.10 mol) at 25° C. The mixture was stirred for 15 minutes, then subjected to vacuum (0.25 mm Hg) for 15 minutes to remove water. Acetic acid (11.87 g, 0.18 mol) was added to bring the pH to about 3.8. 2-Ethylacrolein (10.05 g, 0.12 mol) was added and the reaction mixture was stirred for 5 hours at 105° C. The reaction mixture was cooled to room temperature and the crude product (46.5 g) analyzed by NMR. The analysis showed that the reaction proceeded with 95% conversion to give diethyl 5-EPDC in about 40% yield (based on external standard).

EXAMPLE 31

Synthesis of Dibutyl 5-EPDC from Hydroxylamine, Dibutyl Maleate, and 2-Ethylacrolein Hydroxylamine free base (50% aqueous solution, 8.0 g, 0.12 mol) was added dropwise to dibutyl maleate (25.0 g, 0.1 mol) in a 3-necked 250-ml flask blanketed with nitrogen. The reaction temperature was maintained below 55° C. with an ice bath. The mixture was stirred for 30 minutes and then analyzed by NMR, which indicated 96% conversion of dibutyl maleate to dibutyl N-hydroxyaspartate. Butanol (29.8 g), hexadecane (0.98 g), 2-ethylacrolein (10.0 g, 0.12 mol), and trifluoroacetic acid (2.0 g, 0.018 mol) were added in succession to the reaction mixture, which was then stirred at 90°-95° C. for 4.5 hours under nitrogen. The reaction mixture was cooled to room temperature and analyzed with hexadecane as an internal standard. The analysis showed that the reaction had proceeded with 82% conversion (based on dibutyl maleate) and 45% selectivity to dibutyl 5-EPDC. The solvent was removed under reduced pressure to give the crude product (37.8 g) which was purified by vacuum distillation to give dibutyl 5-EPDC (14.0 g, 35% yield).

EXAMPLE 32

Preparation of Diethyl 5-EPDC from Hydroxylamine Sulfate

Sodium hydroxide (40% aqueous solution, 13.0 g, 0.13 mol) was added over 15 minutes to a mixture of diethyl maleate (17.3 g, 0.100 mol) and hydroxylamine sulfate (25% aqueous solution, 39.10 g, 0.060 mol). The reaction temperature increased from 29° C. to 45° C. during the addition. After the reaction mixture had been stirred under nitrogen for an additional 30 minutes, 1-butanol (30.5 g) was added. The mixture was transferred to a separatory funnel, the layers were allowed to separate, and the organic layer (55.14 g) containing diethyl N-hydroxyasparate was collected. The pH of the organic layer was found to be 7.3. Acetic acid (7.4 g, 0.123 mol) was added to the crude product from the above reaction to adjust the pH to 3.8. Ethylacrolein (9.84 g, 0.11 mol) was added dropwise to the reaction mixture over 15 minutes at room temperature. The reaction was slowly warmed to 95°-96° C., stirred at this temperature for 20 hours, and then was concentrated under reduced pressure to give crude diethyl 5-EPDC (26.19 g). GLC analysis of this crude product indicated that the reaction had proceeded with 93% conversion to give diethyl 5-EPDC in about 51% yield.

EXAMPLE 33

Preparation of Diethyl 5-EPDC from Hydroxylamine Sulfate in Toluene

Sodium hydroxide (40% aqueous solution, 13.0 g, 0.13 mol) was added over 35 minutes to a mixture of diethyl maleate (17.3 g, 0.100 mol) and hydroxylamine sulfate (25% aqueous solution, 39.20 g, 0.060 mol). During the addition, the reaction temperature increased from 26° C. to 55° C. After the reaction mixture had been stirred under nitrogen for 30 additional minutes, after which toluene (36 mL) was added. The mixture was transferred to a separatory funnel, the layers were allowed to separate, and the organic layer (49.08) containing diethyl N-hydroxyaspartate was collected. The pH of the organic layer was found to be 6.6. Acetic acid (6.4 g, 0.106 mol) was added to the crude product from the above reaction to lower the pH to 3.0. Ethylacrolein (9.88 g, 0.11 mol) was added dropwise to the reaction mixture over 15 minutes at room temperature. The pH of the resulting mixture was 3.3. The reaction mixture was warmed slowly to 79°-80° C., stirred at this temperature for 20 hours, and then concentrated under reduced pressure to give crude diethyl 5-EPDC (25.67 g). GLC analysis of this crude product indicated that the reaction had proceeded with 94% conversion to give diethyl 5-EPDC in about 41% yield.

EXAMPLE 34

Procedure without added Acid catalyst

Hydroxylamine free base (50% aqueous solution, 8.0 g, 0.12 mol) was added dropwise to diethyl maleate (17.4 g, 0.10 mol). The reaction mixture temperature was maintained below 55° C. with an ice bath. The mixture was stirred for 30 minutes at room temperature (pH 7.35). Ethanol (35 g) and 2-ethylacrolein (9.8 g, 0.12 mol) were added to the reaction mixture. The pH of the reaction mixture was measured (6.75) and then the reaction mixture was refluxed for 20 hours under nitrogen. The mixture was cooled to room temperature and concentrated under reduced pressure to give 40.9 g of crude product. GLC analysis indicated 96% conversion of the diethyl maleate feed. Products included diethyl 2-aminomaleate (14.7%), diethyl hexahydro-5-EPDC (1.1%), diethyl 5-EPDC (21.8%), and diethyl tetrahydro-5-EPDC (2.1%).

EXAMPLES 35-63

The general procedure of Example 20 was repeated while varying solvent, catalyst, temperature, time, pH, and moles of reactants. Complete operating parameters and results are shown in Table II:

TABLE II

| | | | | Preparation of Diethyl 5-EPDC | | | | | | | | |
|---|---|---|---|---|---|---|---|---|---|---|---|---|
| Ex. Mo | Moles DEM | Moles MM20H | Moles 2-EtAcr | Acid Name/g | Addit. Name/g | Solvent Name/g | Temp °C. | Time hrs | RX pH | Conv % | Anal KDPC | Yield (%) 4H-EPDC |
| 35. | 0.099 | 0.133 | 0.134 | HOAc/15 | | EtOH/37.8 | 82 | 5.4 | 3.7 | 97.8 | 41.6 | 5.4 |
| 36. | 0.100 | 0.133 | 0.133 | HOAc/15 | | MoCN/30.0 | 65 | 5.3 | 3.5 | 98.0 | 36.1 | 11.9 |
| 37. | 0.025 | 0.030 | 0.024 | HOAc/2.1 | BQ/.2 | — | 100 | 5.0 | 4.4 | 98.4 | 34.7 | 3.2 |
| 38. | 0.024 | 0.031 | 0.032 | TFA/1.0 | | EtOH/15.0 | 70-80 | 3.5 | 3.1 | 91.8 | 47.7 | 7.3 |
| 39. | 0.025 | 0.031 | 0.032 | TFA/1.0 | Pd—C/.3 | — | 90-100 | 6.0 | 3.1 | 93.9 | 41.3 | 0.0 |
| Temperature | | | | | | | | | | | | |
| 40. | 0.100 | 0.121 | 0.120 | TFA/1.1 | | EtOH/49.0 | 50 | 5.0 | 4.0 | 88.8 | 15.5 | 1.0 |
| 41. | 0.101 | 0.139 | 0.135 | HOAc/15 | | EtOH/37.8 | 70 | 5.8 | 4.1 | 96.9 | 39.2 | 11.4 |
| 42. | 0.025 | 0.031 | 0.035 | TFA/1.5 | | EtOH/11.8 | 78 | 3.0 | 2.9 | 96.0 | 45.9 | 1.0 |
| 43. | 0.024 | 0.030 | 0.030 | TFA/2.8 | | — | 90 | 5.0 | 3.0 | 96.7 | 39.5 | 0.0 |
| 44. | 0.100 | 0.121 | 0.119 | TFA/4.6 | | — | 100 | 4.0 | 3.1 | 94.0 | 44.3 | 0.0 |
| Acids | | | | | | | | | | | | |
| 45. | 0.025 | 0.032 | 0.032 | TFA/1.2 | | — | >100 | 4.0 | 3.1 | >99.0 | 36.9 | <1.0 |
| 46. | 0.101 | 0.102 | 0.119 | HOAc/5.1 | | — | >100 | 5.5 | 3.8 | 98.8 | 38.9 | 1.0 |
| 47. | 0.054 | 0.030 | 0.032 | $H_2SO_4$/.45 | | EtOH/15.0 | 80 | 4.5 | 1.6 | 92.5 | 31.6 | 3.0 |
| 48. | 0.051 | 0.065 | 0.068 | $H_2SO_4$ | | EtOH/39.5 | 82 | 2.3 | 1.9 | >99.0 | 22.2 | 6.3 |
| 49. | 0.099 | 0.131 | 0.132 | p-TSA | | EtOH/30.0 | 82 | 4.3 | 3.0 | 66.4 | 9.6 | 1.5 |
| 50. | 0.101 | 0.131 | 0.133 | p-TSA | | EtOH/30.0 | 82 | 4.0 | 3.0 | 73.1 | 19.6 | 2.5 |
| 51. | 0.024 | 0.030 | 0.033 | PhOH/2.3 | | — | 100 | 6.0 | 5.2 | 94.6 | 45.8 | 3.8 |
| 52. | 0.024 | 0.029 | 0.029 | DEAHC/2.6 | | EtOH/15.0 | 78 | 4.0 | 5.0 | 76.7 | 27.2 | 2.1 |
| Solvents | | | | | | | | | | | | |
| 53. | 0.024 | 0.030 | 0.027 | TFA/1.0 | | C6H6/10.0 | 65 | 4.0 | 3.4 | 95.8 | 44.9 | 0.0 |
| 54. | 0.024 | 0.025 | 0.027 | TFA/0.5 | | C6H6/20.0 | 80 | 20.0 | 4.0 | 93.6 | 41.4 | 0.0 |
| 55. | 0.100 | 0.131 | 0.133 | HOAc/15 | | EtOH/37.8 | 82 | 5.3 | 3.8 | 99.0 | 68.0 | 12.2 |
| 56. | 1.000 | 1.306 | 1.321 | HOAc/267 | | EtOH/300 | 82 | 5.0 | 3.5 | 90.8 | 42.3 | 6.3 |
| 57. | 1.014 | 1.320 | 1.324 | HOAc/137 | | EtOH/300 | 82 | 5.2 | 3.6 | 98.2 | 44.8 | 3.4 |
| 58. | 1.000 | 1.100 | 1.30 | HOAc/114 | | MoCN/300 | 83 | 5.3 | 3.6 | 95.4 | 41.3 | 9.1 |

TABLE II-continued

Preparation of Diethyl 5-EPDC

| Ex. Mo | Moles DEM | Moles MM2OH | Moles 2-EtAcr | Acid Name/g | Addit. Name/g | Solvent Name/g | Temp °C. | Time hrs | RX pH | Conv % | Anal KDPC | Yield (%) 4H-EPDC |
|---|---|---|---|---|---|---|---|---|---|---|---|---|
| 59. | 0.100 | 0.131 | 0.133 | HOAc/15 | | Digly/38.0 | 105 | 3.0 | 3.8 | 98.2 | 37.4 | <0.7 |
| Time | | | | | | | | 19.0 | | | 40.8 | |
| 60. | 0.100 | 0.133 | 0.133 | HOAc/20 | | EtOH/37.8 | 70 | 3.5 | 3.5 | 95.5 | 34.1 | 12.5 |
| | | | | | | | | 19.5 | | 98.9 | 44.6 | 8.9 |
| 61. | 0.099 | 0.134 | 0.131 | HOAc/15 | | EtOH/37.8 | 70 | 3.0 | 3.4 | 94.8 | 30.9 | 8.3 |
| | | | | | | | | 19.5 | | 98.6 | 40.5 | 7.3 |
| 62. | 0.100 | 0.110 | 0.130 | HOAc/15 | | MoCN/30.0 | 65 | 4.0 | 3.73 | 96.4 | 42.6 | 11.1 |
| | | | | | | | | 19.0 | | 96.9 | 49.3 | 10.4 |
| 63. | 0.100 | 0.131 | 0.133 | HOAc/15 | | EtOH/37.8 | 82 | 5.0 | 3.7 | 93.3 | 37.8 | 7.6 |

Conversions and yields were determined by capillary gas chromatography using either an internal standard (n-hexadecane) or an external standard.
Notes:
In Examples 38 and 47, the reaction mixture was stirred at room temperature over 3 days.
Example 39 and 51, the reaction mixture was stirred at room temperature overnight.
In Example 41, air was sparged through the reaction mixture.
In Examples 48–50, some insoluble salt was formed.
In Example 63, diethyl fumarate was used.
Acronyms:
DEM = Diethyl maleate
2-EtAcr = 2-Ethylacrolein
Addit = Additive
Rx = Reaction
EPDC = Diethyl 5-Ethylpyridine-2,3-dicarboxylate
4H-EPDC = Diethyl tetrahydro-5-ethylpyridine-2,3-carboxylate
TFA = Trifluoroacetic acid
BQ = Benzoquinone
p-TSA = p-toluenesulfonic acid
DEAHC = Diethylamine hydrochloride

EXAMPLE 64

Addition of Ethanol to Aqueous Solution Prepared from Hydroxylamine Sulfate and Sodium Hydroxide to Produce a Homogeneous Reaction Mixture A solution of 394.4 g (0.60 mole; 1.20 eq) of 25% aqueous hydroxylamine sulfate was placed in a 2-liter round-bottom flask equipped with a reflux condenser, thermometer, dropping funnel, mechanical stirrer, and cooling bath. To this was added over about a thirty minute period, 94.1 g (1.20 mole) of 50% aqueous sodium hydroxide. Phenolphthalein indicator was added and the last of the caustic was added dropwise to the end point (pH of ~9.5). The temperature was kept below 40° C. Then 400 mL of ethanol was added and the precipitated sodium sulfate was removed by filtration. Then 172.0 (1 mole) of diethyl maleate was added and resulting homogeneous solution was stirred for 30 minutes. The cooling bath was replaced with a heating mantle. Acetic acid (125 mL) was added to lower the pH from 6.76 to 4.1. Finally, 122.5 g (1.3 mole of 90% purity) of 2-ethylacrolein was added at room temperature over 30 minutes and then the mixture was heated to 80° C. and stirred for 3 hours. A sample was taken for analysis. The reaction mixture was stirred ovenight at 80° C. and resampled. The Et 5-EPDC yield was 48.8% after overnight heating; 40.9% after 3 hours.

EXAMPLE 65

Example 64 was repeated except that the reaction temperature was increased to 88° C. (reflux) and the reaction was repeated. The Et 5-EPDC yield was 48.1% after overnight heating; 43.5% after 3 hours.

EXAMPLE 66

Example 65 was repeated except that about half of the sodium sulfate present was precipitated and recovered by filtration. The Et 5-EPDC yield was 47.0% after overnight heating.

EXAMPLE 67

Example 67 was repeated with methanol in place of ethanol. The reflux temperature was 81° C. The Et 5-EPDC yield was 48.8% after overnight heating but only 18.8% after 3 hours.

EXAMPLE 68

Synthesis of 5-Ethyl-2-(5-isopropyl-5-methyl-4-oxo-2-imidazolin-2-yl) Nicotinic Acid from 5-EPDC Anhydride 2-Amino-2,3-dimethylbutyramide (0.80 g, 6.1 mmol) was added to a solution of 5-ethylpyridine-2,3-dicarboxylic acid anhydride (1.02 g, 5.80 mmol) in anhydrous tetrahydrofuran (8 mL). The reaction mixture was stirred for 24 hours at room temperature under nitrogen and concentrated under reduced pressure to afford light brown material. Sodium hydroxide (6M solution, 8 mL) was added to the brown residue and stirred for four hours at 70° C. The reaction mixture was cooled to room temperature and sulfuric acid was added (3M solution, 7 mL) to bring pH to 8.76. The reaction mixture was extracted twice with diethyl ether (25 mL each). The organic extracts were discarded. The sulfuric acid was added to the aqueous layer to bring the pH to 3.0, upon which the product precipitated as white crystals. The product, 5-ethyl-2-(5-isopropyl-5-methyl-4-oxo-2-imidazolin-2-yl), was filtered and dried (1.12 g, 67% yield). The product was characterized by proton NMR.

What is claimed is:
1. A method for the preparation of a N-hydroxy-2-aminobutane diacid derivative of the formula

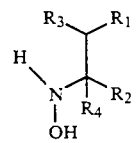

wherein $R_1$ and $R_2$ are each independently

wherein Z is $OR_5$ or $NR_5R_6$; or CN; or
wherein $R_1$ and $R_2$ together is

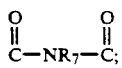

wherein $R_3$ and $R_4$ are each independently H; alkyl; substituted and unsubstituted aryl, wherein said substituents are selected from alkyl, arylalkyl, alkoxy, carboxy, halogen, nitro, and cyano;

wherein Z is defined as above; CN; or halogen;
wherein $R_5$ and $R_6$ are each independently H, alkyl, aryl, arylalkyl;
or wherein $R_5$ and $R_6$ together with the nitrogen atom form a heterocyclic substituent selected from pyrrolidinyl, piperidinyl, imidazolidyl, and hydrogenated pyrimidinyl;
wherein $R_7$ is H, alkyl, aryl, or an alkoxy of 1–6 carbon atoms; which method comprises the steps of:
 a) providing a first compound of the formula

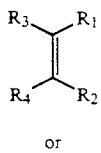

or

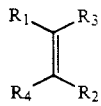

or an isomer thereof, wherein $R_1$, $R_2$, $R_3$, and $R_4$ are defined as above,
 b) contacting said first compound with an unsubstituted hydroxylamine of the formula $NH_2$—OH, or a suitable salt thereof, in a reaction medium having a pH ranging from about 5 to about 12.

2. The method of claim 1, wherein said pH ranges from about 6.5 to about 9.

3. The method of claim 1, wherein said reaction medium includes a solvent selected from the group consisting of water, a $C_1$–$C_6$ alkanol, a halogenated $C_1$–$C_6$ hydrocarbon, an aromatic hydrocarbon, an ether, an ester, an aprotic solvent, and mixtures thereof.

4. The method of claim 1, wherein said first compound is selected from the group consisting of diethyl maleate, dimethyl maleate, dibutyl maleate, dimethyl fumarate, diethyl fumarate, dibutyl fumarate, fumaronitrile, and triethylethanetricarboxylate.

5. The method of claim 1, wherein said suitable salt of said unsubstituted hydroxylamine of said formula is used in combination with a suitable base.

6. The method of claim 5, wherein said suitable salt comprises a sulfate or a hydrochloride and wherein said suitable base is selected from sodium hydroxide or potassium hydroxide.

7. The method of claim 1, wherein said unsubstituted hydroxylamine is provided in the form of an organic solvent solution, whereby a homogenous reaction between said hydroxylamine and said first compound is carried out.

8. The method of claim 7, wherein said organic solvent solution of said unsubstituted hydroxylamine is prepared by reacting a salt of said unsubstituted hydroxylamine with an inorganic base, followed by the addition of an organic solvent and filtration of the resulting mixture to remove an inorganic salt, leaving as a filtrate said organic solvent solution of said unsubstituted hydroxylamine.

9. The method of claim 1, wherein said unsaturated first compound is dimethyl maleate and said unsubstituted hydroxylamine is hydroxylamine or a suitable salt thereof, to prepare dimethyl N-hydroxyaspartate.

10. The method of claim 1, wherein said unsaturated first compound is diethyl maleate and said unsubstituted hydroxylamine is hydroxylamine or a suitable salt thereof to prepare diethyl N-hydroxyaspartate.

11. The method of claim 1, wherein said unsaturated first compound is dibutyl maleate and said unsubstituted hydroxylamine is hydroxylamine or a suitable salt thereof to prepare dibutyl N-hydroxyaspartate.

12. The method of claim 1, wherein said unsaturated first compound is fumaronitrile and said unsubstituted hydroxylamine is hydroxylamine or a suitable salt thereof to prepare N-hydroxyaspartonitrile.

13. The method of claim 1, wherein said unsaturated first compound is triethyl ethene-1,1,2-tricarboxylate and said unsubstituted hydroxylamine is hydroxylamine or a suitable salt thereof to prepare triethyl-2 (N-hydroxyamino)-ethane-1,1,2-tricarboxylate.

14. A method for the preparation of pyridine derivatives having the formula

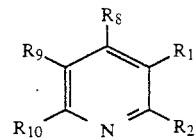

wherein $R_1$ and $R_2$ are each independently CN or

or wherein one of $R_1$ and $R_2$ is CN or

and the other of $R_1$ and $R_2$ is H, alkyl, aryl; or wherein $R_1$ and $R_2$ together is

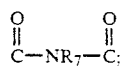

wherein Z is $OR_5$ or $NR_5R_6$;
wherein $R_5$ and $R_6$ are each independently H, alkyl, aryl, arylalkyl, or $R_5$ and $R_6$ together with the nitrogen atom form a heterocyclic substituent selected from pyrrolidinyl, piperidinyl, imidazolidyl, and hydrogenated pyrimidinyl;
wherein $R_7$ is H, alkyl, substituted or unsubstituted phenyl, or alkoxy; wherein $R_8$ and $R_{10}$ are H, alkyl, alkenyl, or substituted or unsubstituted aryl, wherein said substituent is selected from alkyl, alkoxy, carboxy, carboalkoxy, halogen, and cyano;
wherein $R_9$ is the same as $R_8$ and $R_{10}$ above, but also including halogen, and wherein $R_9$ and $R_{10}$ taken together can be $—(CH_2)—_{3-10}$; which method comprises the steps of:

a) providing an N-hydroxy-2-aminoethane derivative of the formula

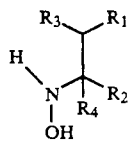

wherein $R_1$ and $R_2$ are as described above, wherein $R_3$ is H or halogen, and wherein $R_4$ is H; and b) contacting said N-hydroxy-2-aminoethane derivative with an α,β-unsaturated carbonyl compound of the formula

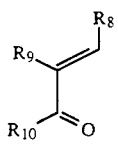

wherein, $R_8$, $R_9$, and $R_{10}$ are defined as above, in the presence of a reaction medium comprising an acid at a temperature ranging from about 25° C. to about 150° C. at the contacting pressure, until the reaction is essentially complete.

15. The method of claim 14, wherein said reaction medium also comprises a solvent, and wherein said reaction temperature ranges from about 25° C. to the boiling point of said solvent.

16. The method of claim 14 or claim 15, wherein a dehydrogenation catalyst is added to said reaction medium to aid in aromatization of the pyridine ring structure.

17. The method of claim 16, wherein said dehydrogenation catalyst comprises a metal or metal compound selected from the group consisting of platinum, palladium, ruthenium, iridium, nickel, iron, copper, cobalt, rhodium, and combinations thereof.

18. The method of claim 17, wherein said metal or metal compound is on a support selected from the group consisting of alumina, carbon, clay, zeolites, chromia, and zironia.

19. The method of claim 18, wherein said dehydrogenation catalyst is palladium on a carbon support.

20. The method of claim 14, wherein the solvent is a lower alkyl alcohol.

21. The method of claim 20, wherein the solvent is 1-butanol.

22. The method of claim 14 or claim 15, wherein the reaction is carried out at a pH of 2-7.

23. The method of claim 22, wherein the reaction is carried out at a pH of 3-4.

24. The method of claim 14 or claim 15, wherein the N-hydroxyamino derivative is diethyl N-hydroxyaspartate.

25. The method of claim 14 or claim 15, wherein the unsaturated carbonyl compound is 2-ethylacrolein.

26. The method of claim 14 or claim 15, for the preparation of diethyl 5-ethylpyridine-2,3-dicarboxylate.

27. The method of claim 14 or claim 15, for the preparation of diethyl 5-methylpyridine-2,3-dicarboxylate.

28. The method of claim 14 or claim 15, for the preparation of diethyl 6-ethylpyridine-2,3-dicarboxylate.

29. The method of claim 14 or claim 15, for the preparation of diethyl 6-methylpyridine-2,3-dicarboxylate.

30. The method of claim 14 or claim 15, for the preparation of diethyl 4-methylpyridine-2,3-dicarboxylate.

31. The method of claim 14 or claim 15, for the preparation of diethyl pyridine-2,3-dicarboxylate.

32. The method as defined in claim 14 or claim 15, wherein $R_1$ and $R_2$ are each COOH; and which further comprises reacting said 2,3-substituted pyridine compound with a 2-aminoalkanecarboxamide of the formula

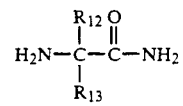

under essentially anhydrous conditions, wherein $R_{12}$ and $R_{13}$ are each independently of the other $C_1$-$C_4$ alkyl, to obtain a compound of the formula

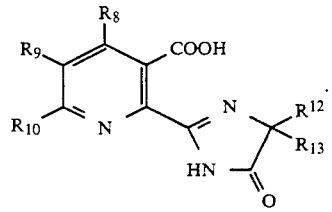

33. The method as defined in claim 14 or claim 15, wherein $R_1$ and $R_2$ are each COOH; and which further comprises reacting said 2,3-substituted pyridine compound with an aminonitrile of the formula

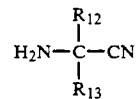

where $R_{12}$ and $R_{13}$ are each independently of the other $C_1$-$C_4$ alkyl, to obtain a compound of the formula

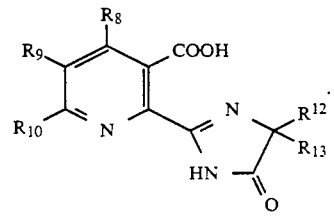

34. A method for the preparation of pyridine derivatives having the formula

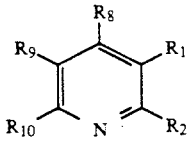

wherein $R_1$ and $R_2$ are each independently CN or

or wherein one of $R_1$ and $R_2$ is CN or

and the other of $R_1$ and $R_2$ is H, alkyl, aryl; or wherein $R_1$ and $R_2$ together is

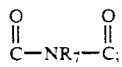

wherein Z is $OR_5$ or $NR_5R_6$;
wherein $R_5$ and $R_6$ are each independently H, alkyl, aryl, arylalkyl, or $R_5$ and $R_6$ together with the nitrogen atom form a heterocyclic substituent selected from pyrrolidinyl, piperidinyl, imidazolidyl, and hydrogenated pyrimidinyl;
wherein $R_7$ is H, alkyl, substituted or unsubstituted phenyl, or alkoxy; wherein $R_8$ and $R_{10}$ are H, alkyl, alkenyl, or substituted or unsubstituted aryl, wherein said substituent is selected from alkyl, alkoxy, carboxy, carboalkoxy, halogen, and cyano;
wherein $R_9$ is the same as $R_8$ and $R_{10}$ above, but also including halogen, and
wherein $R_9$ and $R_{10}$ taken together can be $-(CH_2)-_{3\text{-}10}$;
which method comprises the steps of:
 a) providing an unsaturated carboxylic acid derivative of the formula

or

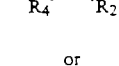

or an isomer thereof, wherein $R_1$ and $R_2$ are as defined above;
wherein $R_3$ is H or halogen;
wherein $R_4$ is H; and
 b) contacting said unsaturated carboxylic acid derivative with hydroxylamine of the formula or a suitable salt thereof, in a reaction medium having a pH ranging from about 5 to about 12, whereby an N-hydroxy-2-aminoethane diacid derivative is formed; and
 c) contacting said N-hydroxy-2-aminoethane carboxylic acid derivative with an α,β-unsaturated carbonyl compound of the formula

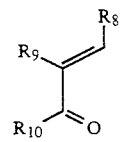

wherein, $R_8$, $R_9$, and $R_{10}$ are defined as above, in the presence of a reaction medium comprising an acid and a solvent at a temperature ranging from about 25° C. to about 150° C., at the contacting pressure, until the reaction is essentially complete.

35. The method of claim 34, wherein said reaction medium also comprises a $C_{1\text{-}6}$-alkyl alcohol solvent, and wherein said reaction temperature ranges from about 25° C. to the boiling point of said solvent.

36. The method of claim 34 or claim 35, wherein said unsubstituted hydroxylamine is provided in the form of an organic solvent solution, wherein the reaction between said hydroxylamine and said unsaturated carboxylic acid derivative is carried out.

37. The method of claim 35, wherein said solvent is a 1-butanol.

38. The method of claim 34 or claim 35, wherein said contacting is carried out in said reaction medium at a pH ranging from about 2 to about 7.

39. The method of claim 38, wherein said pH ranges from about 3 to about 4.

40. The method of claim 34 or claim 35, wherein a dehydrogenation catalyst is added to said reaction medium in step c) to aid in aromatization of the pyridine ring structure.

41. The method of claim 34 or claim 35, wherein said method is carried out in a series of steps without the isolation of major intermediary products.

* * * * *